(12) United States Patent
Chiang

(10) Patent No.: US 11,730,851 B2
(45) Date of Patent: Aug. 22, 2023

(54) LIMB IMMOBILIZATION DEVICE

(71) Applicant: Hui-Yi Chiang, Zhubei (TW)

(72) Inventor: Hui-Yi Chiang, Zhubei (TW)

( * ) Notice: Subject to any disclaimer, the term of this patent is extended or adjusted under 35 U.S.C. 154(b) by 525 days.

(21) Appl. No.: 16/945,939

(22) Filed: Aug. 3, 2020

(65) Prior Publication Data

US 2021/0038756 A1 Feb. 11, 2021

(30) Foreign Application Priority Data

Aug. 5, 2019 (TW) .................. 108210318

(51) Int. Cl.
  *A61L 15/14* (2006.01)
  *A61L 15/12* (2006.01)

(52) U.S. Cl.
  CPC ............ *A61L 15/14* (2013.01); *A61L 15/125* (2013.01)

(58) Field of Classification Search
  CPC .......... A61F 5/01–0118; A61F 5/04–05; A61F 5/058; A61F 5/05825–05875; A61F 5/10; A61F 5/37; A61F 5/3723; A61F 5/013; A61F 5/05858–05875
  See application file for complete search history.

(56) References Cited

U.S. PATENT DOCUMENTS

| | | | |
|---|---|---|---|
| 6,482,167 B2* | 11/2002 | Grim | A61F 13/04 602/8 |
| 8,790,287 B2* | 7/2014 | Evans | D04B 21/16 602/76 |
| 9,877,872 B2* | 1/2018 | Mumby | A61F 13/0203 |
| 2014/0182603 A1* | 7/2014 | Coppens | A61L 31/06 128/869 |
| 2019/0254361 A1* | 8/2019 | Gorissen | A41D 1/04 |
| 2019/0284742 A1* | 9/2019 | Rwei | B29B 15/122 |

FOREIGN PATENT DOCUMENTS

| | | | | |
|---|---|---|---|---|
| CN | 103892948 | | 7/2014 | |
| DE | 19722118 A1 | * | 2/1999 | ............ A61F 5/0111 |
| EP | 1004829 A1 | * | 5/2000 | ............ A61G 7/0573 |
| GB | 2534181 | * | 1/2015 | ......... A41D 13/0537 |
| TW | M577021 U | | 4/2019 | |
| TW | 201938361 A | | 10/2019 | |
| WO | WO-2005052235 A1 | * | 6/2005 | ............ A61F 13/04 |
| WO | WO2012/018785 | | 2/2012 | |

OTHER PUBLICATIONS

Peter Dr Med Schaff and Ewald Berkowitsch, "Ankle supporting device used as plaster substitute" May 1997, All Pages (Year: 1997).*

* cited by examiner

*Primary Examiner* — Alireza Nia
*Assistant Examiner* — Eric Richard McQuiggan
(74) *Attorney, Agent, or Firm* — IPR Works

(57) ABSTRACT

The invention provides a limb immobilization device, being an immobilization device having a thermoplastic fixation plate capable of being shaped on a patient by covering a limb portion of the patient to support and/or immobilize that portion of the patient. The limb immobilization device has high air permeability and may replace or assist in use of the traditional plaster cast. The thermoplastic fixation plate is a laminate comprising a soft cloth and a first spacer fabric having a coating layer thereon.

14 Claims, 5 Drawing Sheets

LIMB IMMOBILIZATION DEVICE

BACKGROUND OF THE INVENTION a. Field of the Invention

The invention relates to a limb immobilization device, in particular to a limb immobilization device with good air permeability which can improve and/or replace traditional plaster casts and can be directly shaped on a patient to fit a specific portion of the patient.

b. Description of the Related Art

Limb immobilization devices can be used as a device for fixing joints and/or supporting fracture sites by covering the parts of the patient that need to be fixed and/or supported. Fixation and/or support of the patient's limbs can help heal or protect injured tissue by restricting unwanted movements. Furthermore, the use of limb immobilization devices can achieve the effect of replacing weak muscles, avoiding increased joint deformation, and preventing scar contractures.

For general fractures, it is to use a plaster cast to fix and/or support parts of the patient that need to be fixed and/or supported. The airtight nature of plaster and lack of accommodation for initial edema at the site of fracture creates patient discomfort. Current alternatives include use of low-temperature thermoplastic and high-temperature thermoplastic splints. Low-temperature thermoplastic splints can be directly formed on a patient. However, at present, to achieve sufficient strength, low-temperature thermoplastic splints require an increased thickness, as a result, increasing the weight of the device. Air permeability is achieved by creating holes penetrating both superficial layers of the device. However, this solution is inefficient, and the problem of insufficient air permeability remains. If the diameter of the penetrating holes is increased, the strength of the device will be compromised. High-temperature thermoplastic splints require the orthotist to take a mold from the target part of the patient. After making the mold, the high-temperature thermoplastic material is wrapped along the contour of the mold and fitted to the mold by vacuum. The orthotist then needs to trim and adjust the newly formed device and add the auxiliary pad and fastening straps before it can be used on the patient.

Therefore, there is a need for an innovative limb immobilization device not only as an orthotic device but also as a splinting device capable of improving and/or replacing conventional plaster casts, low-temperature thermoplastic splints, and high-temperature thermoplastic splints with characteristics of good air permeability and can be directly shaped on the patient while providing patient comfort.

BRIEF SUMMARY OF THE INVENTION

In light of the above background information, in order to fulfill the requirements of the industry, one objective of the invention is to provide a limb immobilization device used for fixing and/or supporting fracture sites that can be shaped directly on a patient, covering parts of the patient that need to be fixed and/or supported, which not only provides good air permeability and comfort, but also provides the option of reshaping after the initial shaping process and the advantage of being easy to produce clinically.

In order to achieve one of the above purposes, all the purposes, or other purposes, one embodiment of the invention provides a limb immobilization device, which can be shaped directly on a patient for fixing and/or supporting fracture sites. The limb immobilization device has a thermoplastic fixation plate capable of being shaped directly on a patient by covering a limb portion of the patient to support and/or immobilize the limb portion of the patient. The thermoplastic fixation plate is a laminate of a soft cloth and a composite comprising a first spacer fabric and a coating layer. The coating layer is composed of thermoplastic polymers or thermoplastic composites. The thermoplastic fixation plate has two main surfaces, namely an upper main surface and a lower main surface. The thermoplastic fixation plate further comprises at least one edge covering member extending from the upper main surface to the lower main surface, covering the edges of the thermoplastic fixation plate.

In one embodiment of the invention, the soft cloth is a second spacer fabric. The second spacer fabric comprises a spacer layer sandwiched by two surface layers. The second spacer fabric has thickness in the range of 0.5 to 2 mm.

In one embodiment of the invention, the composite comprising the first spacer fabric and the coating layer on the surface of the first spacer fabric has thickness in the range of 4 to 8 mm. The spacer layer of the first spacer fabric is composed of monofilaments and the diameter of the monofilaments is in the range of 0.1 to 0.25 mm.

In one embodiment of the invention, the composite comprising the first spacer fabric and the coating layer has a Shore hardness of 55 D or greater and flexural strength of 200 MPa or greater. Flexural strength refers to the bending resistance in the three-point bending test as per ASTM D790 standard (Standard Test Methods for Flexural Properties of Unreinforced and Reinforced Plastics and Electrical Insulating Materials). In the specification of the present invention, a specimen having a ratio of span/length/width/thickness equal to 16/40/4/1 is used, the testing speed is set to 15 mm/min, and the value at the 5% deformation without breaking is the flexural strength.

In one embodiment of the invention, the edge covering member is selected from the group consisting of the following or combination thereof: spacer fabric, elastic fabric, cotton, moisture-wicking fabric, bamboo fabric, and carbon fiber fabric.

In one embodiment of the invention, the edge covering member is attached to the laminate of the thermoplastic fixation plate and the soft cloth using a double-sided adhesive tape, or a hot-melt adhesive, or via stitching.

In one embodiment of the invention, wherein the thermoplastic polymer is polycaprolactone or polyurethane; the thermoplastic polymer has a melting point of 40 to 70° C.; the thermoplastic composite comprises a thermoplastic polymer and a filler; the filler is selected from the group consisting of the following: silicon dioxide, talc, or graphite.

In one embodiment of the invention, the composite comprising the first spacer fabric and the coating layer is formed by pressing a specified amount of the thermoplastic polymer or the thermoplastic composite at a temperature above the melting point of the thermoplastic polymer or thermoplastic composite and then heating and cooling to form the coating layer.

In one embodiment of the invention, the composite comprising the first spacer fabric and the coating layer has a plurality of through-holes penetrating the upper and lower main surfaces of the thermoplastic fixation plate and the composite is air-permeable.

In one embodiment of the invention, the spacer layer is formed by monofilaments; the first spacer fabric has a density of monofilaments larger than the second spacer fabric so as to have a temperature difference between the surface of the soft cloth and the bottom main surface of the thermoplastic fixation plate be 10° C. or greater while the laminate is heated.

In one embodiment of the invention, the limb immobilization device further comprises one fastening member to be combined with the thermoplastic fixation plate for fastening the open ends of the thermoplastic fixation plate or securing the functionality of fixation.

In one embodiment of the invention, the thermoplastic fixation plate further comprises an opening for passing a thumb while the immobilization device is applied to the wrist joint.

In one embodiment of the invention, the laminate of the soft cloth and the composite is formed by pressing or using a hot-melt adhesive which has a melting point near the thermoplastic polymer in the thermoplastic fixation plate.

In the previous embodiment of the invention, the double-sided adhesive tape can be an adhesive transfer tape and the hot-melt adhesive for the edge covering member has a melting point higher than 70° C.

In one embodiment of the invention, wherein the spacer layer is composed of monofilaments; the first spacer fabric has a density of monofilaments larger than the second spacer fabric. That is, the spacer layer of the first spacer fabric is composed of monofilaments, and the spacer layer of the second spacer fabric is also composed of monofilaments; the monofilament density of the first spacer fabric is greater than the monofilament density of the second spacer fabric.

Furthermore, in one embodiment of the invention, the thermoplastic fixation plate may be a laminate of a soft cloth, the composite comprising the first spacer fabric and the coating layer, and a soft cloth, formed in sequence.

According to the present invention, the limb immobilization device is provided to have the merits of directly low-temperature forming on a patient, high air permeability and comfort to quickly achieve support and/or immobilization of the fracture site as a novel device to not only provide the functionalities of the traditional plaster casts, low-temperature thermoplastic splints, high-temperature thermoplastic splints, water-activated splints, and rigid braces, but also provide the function of the rehabilitation device.

DETAILED DESCRIPTION OF THE INVENTION

Figure 1:
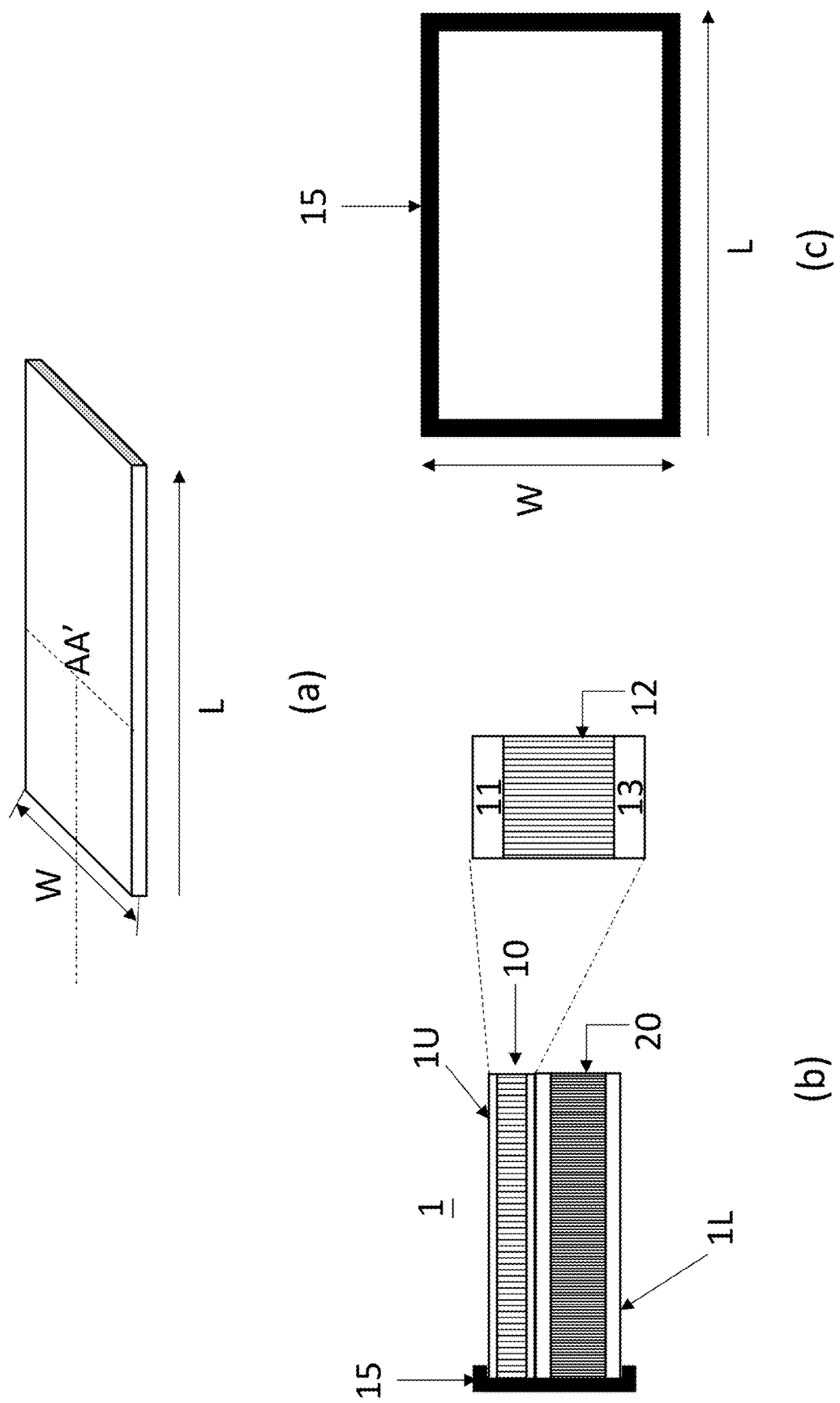
FIG. 1 (a) shows a schematic diagram of a limb immobilization device according to an embodiment of the present invention; (b) shows a cross-sectional schematic diagram taken along line AA' of (a); (c) shows a top-view schematic diagram of (a).

In the following detailed description of the preferred embodiments, reference is made to the accompanying drawings which form a part hereof, and in which are shown by way of illustration, specific embodiments in which the invention may be practiced. The common structures and elements that are known to everyone are not described in detail to avoid unnecessary limits of the invention. In the following examples, the description of the direction, such as upper, lower, left, right, front or rear, etc., is referred to the direction of the drawing. Besides, the meaning of "A layer (or element) is on B layer (element)" includes, but not limited to, "A layer is directly laminated and in contact with B layer". For example, a layer (C layer) may exist between A layer and B layer. Some preferred embodiments of the present invention will now be described in greater detail in the following.

According to an embodiment of the present invention, a limb immobilization device is disclosed, composed of a thermoplastic fixation plate that can be shaped directly on a patient, covering parts of a patient that need to be supported and/or immobilized. The thermoplastic fixation plate is a laminate of a soft cloth and a composite comprising a first spacer fabric and a coating layer. The coating layer is composed of one material selected from the group consisting of the following or combination thereof: thermoplastic polymers and thermoplastic composites. The thermoplastic fixation plate has two main surfaces, namely an upper main surface and a lower main surface. The thermoplastic fixation plate can further comprise at least one edge covering member extending from the upper main surface to the lower main surface, covering the edges of the thermoplastic fixation plate where the upper main surface is one surface of the soft cloth and the lower main surface is the bottom surface of the composite, opposite to the surface in contact with the soft cloth.

Hereinafter, the present invention will be described in greater detail with reference to the drawings.

FIG. 1 (a) shows a schematic diagram illustrating the limb immobilization device 1 according to an embodiment of the invention and FIG. 1 (b) shows a cross-sectional schematic diagram of FIG. 1 (a) taken along line AA' in FIG. 1 (a). FIG. 1 (c) shows a top-view schematic diagram of FIG. 1 (a). In FIG. 1, L represents a direction of the limb immobilization device having a greater flexural strength, referred to as the longitudinal direction, and W represents the direction perpendicular to the longitudinal direction on the main surface of the limb immobilization device 1, referred to as the transverse direction. FIG. 1 (b) shows only one side of the limb immobilization device in the cross-sectional profile of FIG. 1 (a) taken along the line AA' where 15 represents an edge covering member, extending from the upper main surface 1U to the lower main surface 1L, covering the edges of the thermoplastic fixation plate (including the soft cloth 10 and the composite 20 comprising the first spacer fabric and the coating layer). The soft cloth 10 is a spacer fabric (or called three-dimensional fabric) composed of a spacer layer 12 connecting the two surface layers 11 and 13. In FIG. 1, the limb immobilization device has a plurality of through-holes penetrating the upper main surface 1U and the lower main surfaces 1L, providing air permeability.

Figure 2:
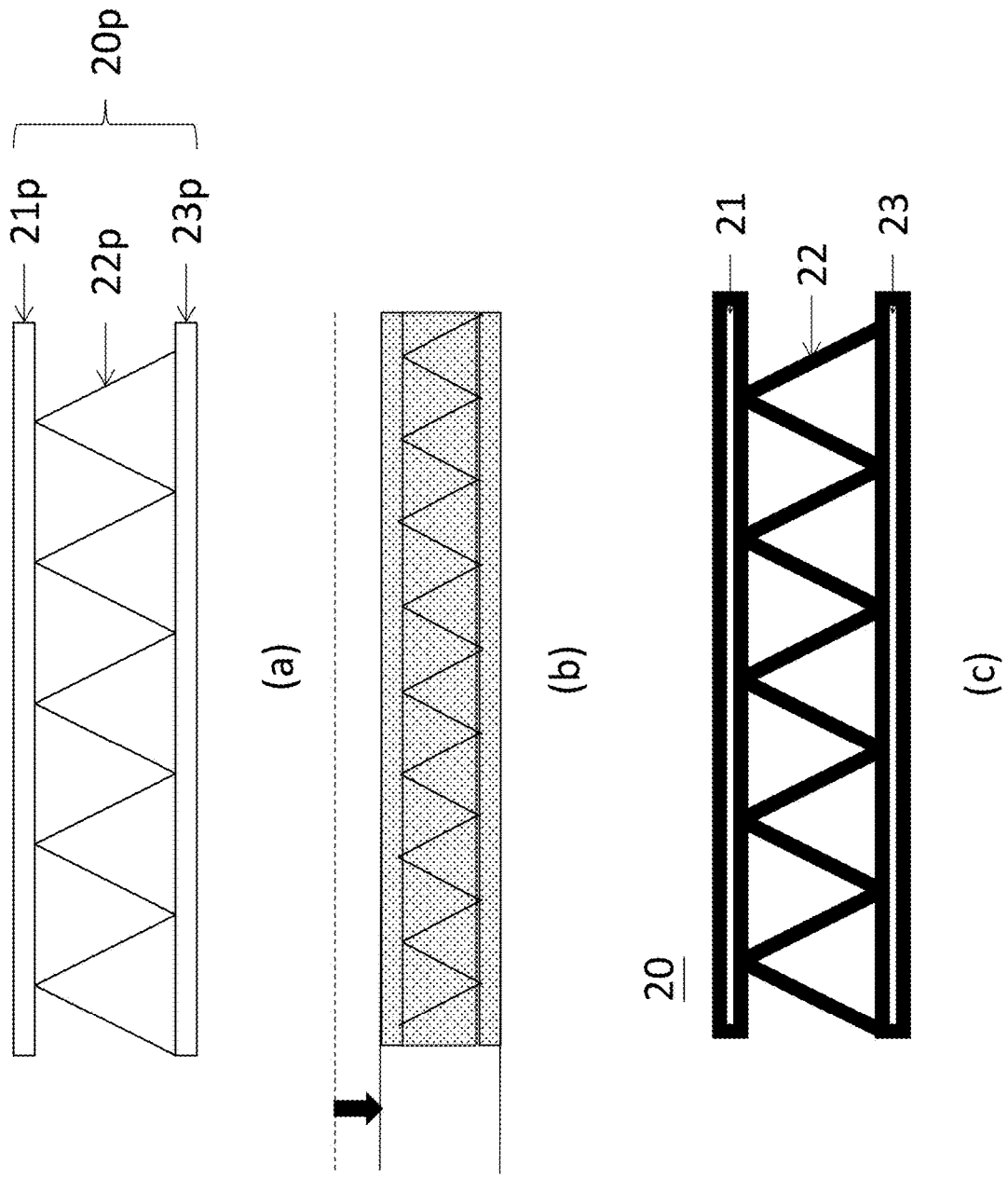
FIG. 2 shows a schematic flow chart illustrating the method of forming the composite comprising a first spacer fabric and a coating layer where (a) shows the first spacer fabric 20p without a coating on the surface; (b) shows the state of combining the material constituting the coating layer and the first spacer fabric; (c) shows the composite comprising the first spacer fabric and the coating layer on the surfaces of the first spacer fabric.

FIG. 2 shows a schematic flow chart illustrating the method of forming the composite comprising the first spacer fabric and the coating layer on the surfaces of the first spacer fabric. FIG. 2 (a) shows a schematic diagram of the first spacer fabric 20p which has no coating on its surface, comprising surface layers 21p, 23p, and spacer layer 22p. FIG. 2 (b) shows a schematic diagram of the state of combining the material constituting the coating layer and the first spacer fabric where the solid downwards arrow indicates that the first spacer fabric 20p is compressed together with the material resulting in the coating layer, having decreased thickness. FIG. 2 (c) shows the composite 20 comprising the first spacer fabric 20p and the coating layer on the surfaces of the first spacer fabric 20p after heating and cooling.

The structure of the composite 20 comprising the first spacer fabric 20p and the coating layer in FIG. 1 (b) is shown in FIG. 2 (c). The composite 20 comprises surface layers 21, 23 and a spacer layer 22. The spacer layer 12 in FIG. 1(b) and the spacer layer 22p in FIG. 2(a) are both composed of monofilaments. The density of monofilaments of the first spacer fabric 20p is greater than that of the soft cloth 10, because the soft cloth 10 has a function of providing heat insulation and comfort to the patient. However, the spacer layer 22p of the first spacer fabric 20p must have a sufficient elastic modulus. That is, it has a compression resistance function providing the composite 20 shown in FIG. 2 (c) sufficient elasticity after compression, heating, and cooling production processes.

Figure 3:
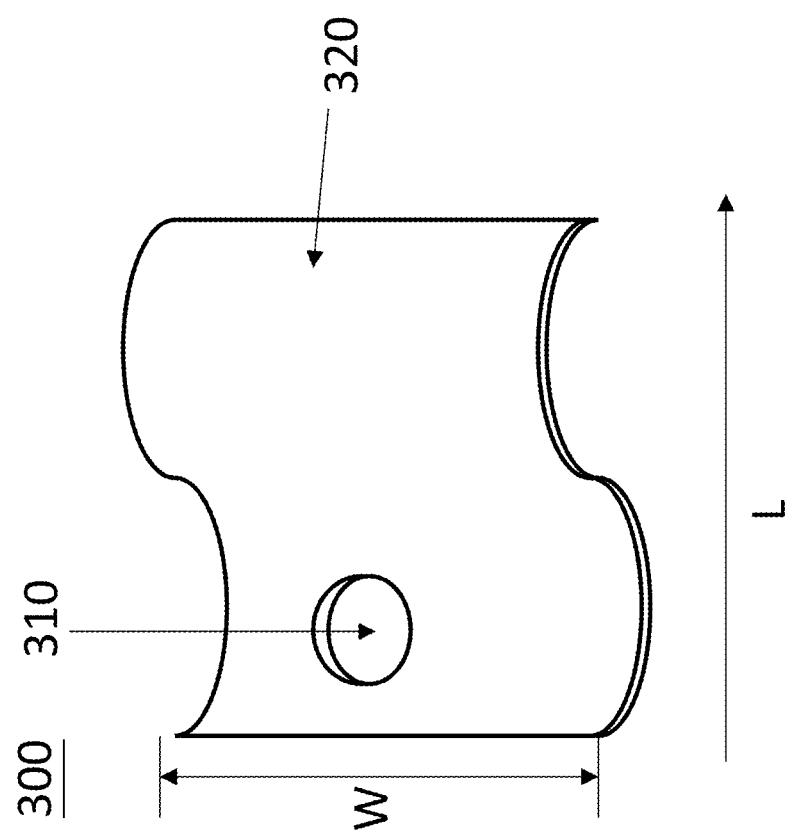
FIG. 3 shows a schematic diagram illustrating a limb immobilization device according to another embodiment of the invention.

FIG. 3 shows a schematic diagram illustrating a limb immobilization device applied to the wrist joint 300 according to another embodiment of the invention. The thermoplastic fixation plate 320 of the limb immobilization device 300 further includes an opening 310. Except for the changes in the shape of the device to better accommodate the wrist joint, all other specifications are the same as the limb immobilization device shown in FIG. 1, and FIG. 3 simply shows the shape of the device. For example, the edge covering member used to cover the edges of the thermoplastic fixation plate 320 and the edges of the opening 310 is not shown in FIG. 3.

Figure 4:
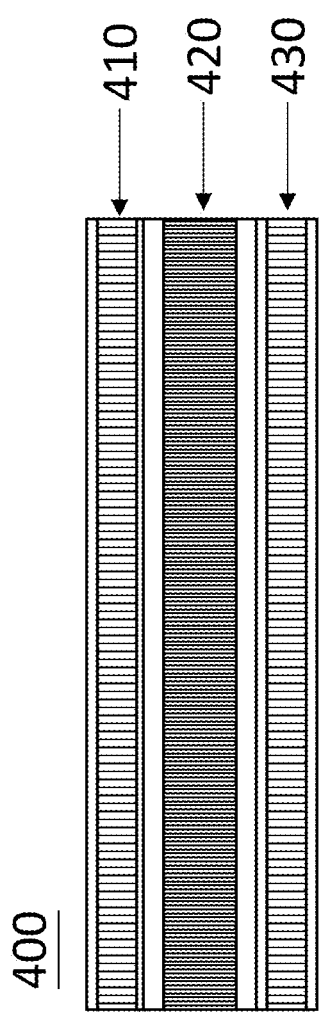
FIG. 4 shows a cross-sectional diagram illustrating a limb immobilization device according to another embodiment of the invention.

FIG. 4 shows a cross-sectional schematic diagram illustrating a limb immobilization device 400 according to another embodiment of the invention where a laminate composed sequentially of the soft cloth 410, the composite 420 comprising the first spacer fabric and the coating layer, and the soft cloth 430. Adhesives may be found between the soft cloth 410 and the composite 420, and between the composite 420 and the soft cloth 430. The limb immobilization device 400 may further include an edge-covering member.

Figure 5:
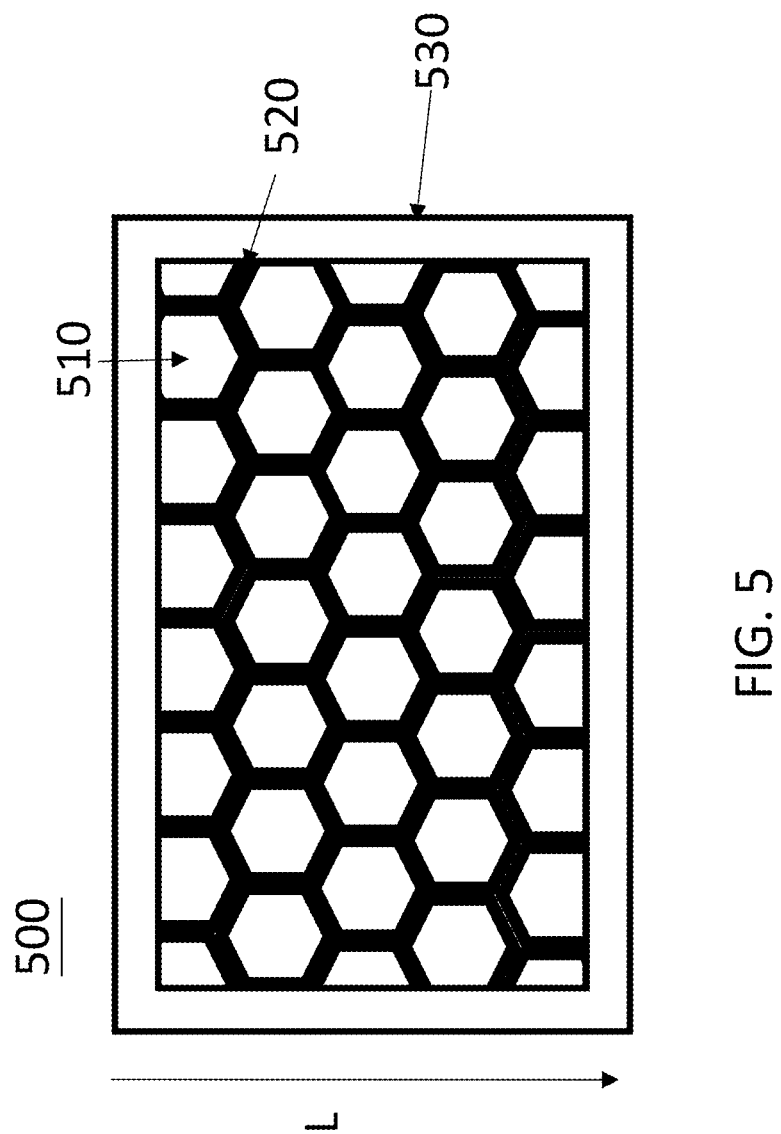
FIG. 5 shows a top-view schematic diagram illustrating a limb immobilization device according to another embodiment of the invention.

FIG. 5 shows a top-view schematic diagram illustrating a limb immobilization device 500 according to another embodiment of the invention, composed of a thermoplastic fixation plate with honeycomb-shaped holes 510, where 520 represents a fiber with a coating layer on the surface thereof constituting the surface layer, and 530 represents the edge covering member, composed of material selected from the group consisting of the following: spacer fabric (three-dimensional fabric), elastic fabric, cotton, moisture-wicking fabric, bamboo fabric, and carbon fiber fabric. The edge covering member may have via-holes or through-holes. The purpose of using the edge covering member is to protect the patient from abrasions caused by the hard edge of the thermoplastic fixation plate. Furthermore, the thermoplastic fixation plate can have various shape depending on its application. Generally, the thermoplastic fixation plate has two axes perpendicular to each other in its main surface, namely longitudinal and transverse axes, having different flexural strengths. The thermoplastic fixation plate can be cut to different shapes to fit the actual needs in flexural strengths. The soft cloth of the limb immobilization device 500 can be spacer fabric, elastic fabric, cotton, moisture-wicking fabric, bamboo fabric, and carbon fiber fabric, as long as it possesses the function of protecting the skin from getting hurt because of the hard surfaces, and air-permeability.

When the soft cloth is a spacer fabric (three-dimensional fabric), it may have one spacer layer, sandwiched by two surface layers, with a total thickness in the range of 0.5 to 2 mm, which may vary depending on the application. The composite comprising the first spacer fabric and the coating layer has a total thickness in the range of 4 to 8 mm, which varies depending on the application. The first spacer fabric has a spacer layer composed of monofilaments with diameter in the range of 0.1 to 0.25 mm, and two surface layers.

Furthermore, the composite comprising the first spacer fabric and the coating layer has a Shore hardness of 55 D or greater and a flexural strength of 200 MPa or greater. Flexural strength refers to the bending resistance in the three-point bending test as per ASTM D790 standard (Standard Test Methods for Flexural Properties of Unreinforced and Reinforced Plastics and Electrical Insulating Materials). In the specification of the present invention, a specimen having a ratio of span/length/width/thickness equal to 16/40/4/1 is used, the testing speed is set to 15 mm/min, and the value at the 5% deformation without breaking is the flexural strength. The flexural strength of the limb immobilization device is preferably in the range of 200 to 400 MPa.

The aforementioned edge covering member is attached to the upper and lower main surfaces of the thermoplastic fixation plate by means of adhesive, double-sided adhesive tape, hot-melt adhesive, or stitches. Furthermore, the double-sided adhesive tape may be a adhesive transfer tape, and the melting point of the hot-melt adhesive for the edge covering member may be 70° C. or higher, and more preferably 200° C. or lower.

The material constituting the coating layer may be a thermoplastic polymer, for example, polycaprolactone or polyurethane, and the thermoplastic polymer may have a melting point of 40 to 70° C. Furthermore, the material constituting the coating layer may be a thermoplastic composite material, for example being a blend of a thermoplastic polymer and a filler where the filler may be silicon dioxide, talc, or graphite.

The material constituting the coating layer of the composite can be thermoplastic polymers or thermoplastic composites. A specified amount of thermoplastic polymers can be applied on the surface of the first spacer fabric by extrusion at a temperature above the melting point of the material. The material and the first spacer fabric together are pressed to form a laminate and then the laminate is heated and cooled to form the coating layer. The specified amount is less than the amount required to fill the empty space of the first spacer fabric. In terms of volume, it is usually 80% or less of the amount of the material needed to fill the holes of the first spacer fabric, preferably 10% to 80%, more preferably 20% to 70%, and even more preferably 30% to 60%.

In the other embodiment, the composite comprising the first spacer fabric and the coating layer can be laminated with the soft cloth using a hot-melt adhesive to form the thermoplastic fixation plate.

The composite comprising the first spacer fabric and the coating layer has a plurality of through-holes. These through-holes penetrate the upper and lower main surfaces of the thermoplastic fixation plate, such that the soft cloth and the composite comprising the first spacer fabric and the coating layer are both air permeable.

The soft cloth also has a heat insulation effect. For example, when the limb immobilization device is heated, the temperature difference between the first spacer fabric side of the thermoplastic fixation plate and the soft cloth side of the thermoplastic fixation plate is 10° C. or greater. That is, the surface of the soft cloth side has a lower surface temperature that can be tolerated by a patient.

According to another embodiment of the invention, the limb immobilization device may further include one or more fastening members bonded and fixed to the thermoplastic fixation plate by hot-melt glue, buttons, and/or stitches for fastening two open ends of the thermoplastic fixation plate together.

The limb immobilization device can be used as a device for fixing joints and/or supporting fracture sites by covering the parts of the patient that need to be supported and/or immobilized to achieve the effect of assisting weak muscles, avoiding increased joint deformation, or preventing scar contractures. When the limb immobilization device is applied to the wrist joint, the thermoplastic fixation plate contains an opening used for passing of the patient's thumb.

According to the present invention, the limb immobilization device is provided to have the merits of directly low-temperature forming on a patient, high air permeability and comfort to quickly achieve supporting and/or immobilizing the fracture site as a novel device to not only provide the functionalities of the traditional plaster casts, low-temperature thermoplastic splints, high-temperature thermoplastic splints, water-activated splints, and rigid braces, but also provide the function of the rehabilitation device.

The foregoing description of the preferred embodiments of the invention has been presented for purposes of illustration and description. It is not intended to be exhaustive or to limit the invention to the precise form or to exemplary embodiments disclosed. Accordingly, the foregoing description should be regarded as illustrative rather than restrictive. Obviously, many modifications and variations will be apparent to practitioners skilled in this art. The embodiments are chosen and described in order to best explain the principles of the invention and its best mode practical application, thereby to enable persons skilled in the art to understand the invention for various embodiments and with various modifications as are suited to the particular use or implementation contemplated. It is intended that the scope of the invention be defined by the claims appended hereto and their equivalents in which all terms are meant in their broadest reasonable sense unless otherwise indicated. Any advantages and benefits described may not apply to all embodiments of the invention. It should be appreciated that variations may be made in the embodiments described by persons skilled in the art without departing from the scope of the invention as defined by the following claims.

What is claimed is:

1. A limb immobilization device, comprising a thermoplastic fixation plate capable of being shaped on a patient by covering a limb portion of the patient to support and/or immobilize the limb portion of the patient, wherein the thermoplastic fixation plate is a laminate of a soft cloth and a composite comprising a first spacer fabric and a coating layer; the coating layer is composed of one material selected from the group consisting of the following or combination thereof: thermoplastic polymers and thermoplastic composites; the thermoplastic fixation plate has two main surfaces, an upper main surface and a lower main surface; the thermoplastic fixation plate further comprises at least one edge covering member extending from the upper main surface to the lower main surface, covering the edges of the thermoplastic fixation plate; the first spacer fabric consists of a spacer layer sandwiched by two surface layers; the spacer layer is formed by monofilaments; and the monofilaments have an average diameter in the range of 0.1 to 0.25 mm; and the soft cloth is a second spacer fabric; the second spacer fabric consists of a spacer layer sandwiched by two surface layers; the spacer layer is formed by monofilaments; the first spacer fabric has a density of monofilaments larger than the second spacer fabric so as to have a temperature difference between the surface of the soft cloth and the lower main surface of the thermoplastic fixation plate be 10° C. or greater while the laminate is heated.

2. The limb immobilization device as claimed in claim 1, wherein the second spacer fabric consisting of a spacer layer sandwiched by two surface layers has a total thickness in the range of 0.5 to 2 mm.

3. The limb immobilization device as claimed in claim 1, wherein the composite comprising the first spacer fabric and the coating layer on the surface of the first spacer fabric has a thickness in the range of 4 to 8 mm.

4. The limb immobilization device as claimed in claim 1, wherein the composite comprising the first spacer fabric and the coating layer on the surface of the first spacer fabric has a Shore hardness of 55D or greater and a flexural strength of 200 MPa or greater.

5. The limb immobilization device as claimed in claim 1, wherein the edge covering member is selected from the group consisting of the following: spacer fabric, elastic fabric, cotton, moisture-wicking fabric, bamboo fabric, and carbon fiber fabric.

6. The limb immobilization device as claimed in claim 1, wherein the edge covering member is attached to the laminate of the thermoplastic fixation plate and the soft cloth using a double-sided adhesive tape or a hot-melt adhesive, or via stitching.

7. The limb immobilization device as claimed in claim 1, wherein the composite comprising the first spacer fabric and the coating layer is formed by pressing a specified amount of the thermoplastic polymer or the thermoplastic composite above the melting temperature of the thermoplastic polymer or the thermoplastic composite and then heating and cooling to form the coating layer.

8. The limb immobilization device as claimed in claim 7, wherein the composite comprising the first spacer fabric and the coating layer has a plurality of through-holes penetrating the upper and lower main surfaces of the thermoplastic fixation plate and the composite is air-permeable.

9. The limb immobilization device as claimed in claim 1, further comprising one fastening member to combine with the thermoplastic fixation plate for fastening open ends of the thermoplastic fixation plate or securing the functionality of fixation.

10. The limb immobilization device as claimed in claim 1, wherein the thermoplastic fixation plate further comprises an opening for passing a thumb while the immobilization device is applied to the wrist joint.

11. The limb immobilization device as claimed in claim 1, wherein the laminate of the soft cloth and the composite is formed by pressing or using a hot-melt adhesive which has a melting point near the thermoplastic polymer in the thermoplastic fixation plate.

12. The limb immobilization device as claimed in claim 6, wherein the double-sided adhesive tape is an adhesive transfer tape and the hot-melt adhesive for the edge covering member has a melting point higher than 70° C.

13. The limb immobilization device as claimed in claim 1, wherein the thermoplastic polymer is polycaprolactone or polyurethane; the thermoplastic polymer has a melting point of 40 to 700 C; the thermoplastic composite comprises a thermoplastic polymer and a filler; the filler is selected from the group consisting of the following: silicon dioxide, talc, and graphite.

14. The limb immobilization device as claimed in claim 1, wherein the thermoplastic fixation plate is a laminate of a soft cloth, the composite comprising the first spacer fabric and the coating layer, and a soft cloth, formed in sequence.

* * * * *